United States Patent [19]

Cohen et al.

[11] Patent Number: 5,700,553
[45] Date of Patent: Dec. 23, 1997

[54] MULTILAYER HYDRODISINTEGRATABLE FILM

[75] Inventors: Bernard Cohen, Berkeley Lake; Lee Kirby Jameson, Roswell; Lamar Heath Gipson, Acworth; Judith Katherine Faass, Dawsonville, all of Ga.

[73] Assignee: Kimberly-Clark Corporation, Neenah, Wis.

[21] Appl. No.: 558,404

[22] Filed: Nov. 16, 1995

[51] Int. Cl.⁶ ................................................ A61F 13/15
[52] U.S. Cl. .................. 428/220; 428/332; 428/337; 428/480; 428/483; 428/532; 428/913; 604/364; 604/366
[58] Field of Search .................................... 428/480, 483, 428/481, 220, 213, 332, 338, 913, 532, 337; 604/364, 365, 366, 372, 370

[56] References Cited

U.S. PATENT DOCUMENTS

| | | | |
|---|---|---|---|
| 3,365,320 | 1/1968 | Minelli | 106/133 |
| 3,526,538 | 9/1970 | Lindemann et al. | 117/140 |
| 3,554,788 | 1/1971 | Fechillas | 117/140 |
| 3,580,253 | 5/1971 | Bernardin | 128/290 |
| 3,890,974 | 6/1975 | Kozak | 128/287 |
| 3,952,347 | 4/1976 | Comerford et al. | 5/335 |
| 4,028,290 | 6/1977 | Reid | 260/17.4 |
| 4,063,995 | 12/1977 | Grossman | 162/112 |
| 4,186,233 | 1/1980 | Krajewski et al. | 428/213 |
| 4,200,558 | 4/1980 | Holst et al. | 260/17 A |
| 4,410,571 | 10/1983 | Korpman | 427/385.5 |
| 4,454,055 | 6/1984 | Richman et al. | 252/194 |
| 4,518,721 | 5/1985 | Dhabhar et al. | 523/120 |
| 4,534,767 | 8/1985 | Habib | 604/336 |
| 4,578,065 | 3/1986 | Habib | 604/336 |
| 4,655,840 | 4/1987 | Wittwer et al. | 106/126 |
| 4,728,325 | 3/1988 | Spiller | 604/372 |
| 4,794,034 | 12/1988 | Nishizawa et al. | 604/372 |

(List continued on next page.)

FOREIGN PATENT DOCUMENTS

| | | |
|---|---|---|
| 2005764 | 6/1990 | Canada . |
| 042259A1 | 12/1981 | European Pat. Off. . |
| 0164197A3 | 12/1985 | European Pat. Off. . |
| 0378940A1 | 7/1990 | European Pat. Off. . |
| 0461484A2 | 12/1991 | European Pat. Off. . |
| 489967A1 | 6/1992 | European Pat. Off. . |
| 499672A1 | 8/1992 | European Pat. Off. . |
| 585906A2 | 3/1994 | European Pat. Off. . |
| 0604730A1 | 7/1994 | European Pat. Off. . |
| 0639381A1 | 2/1995 | European Pat. Off. . |
| 63-304082 | 12/1988 | Japan . |
| 3020364 | 1/1991 | Japan . |
| 3095211 | 4/1991 | Japan . |
| 5086344 | 4/1993 | Japan . |
| 6057059 | 3/1994 | Japan . |
| 1379660 | 1/1975 | United Kingdom . |
| 2048078 | 12/1980 | United Kingdom . |
| 2246373 | 1/1992 | United Kingdom . |
| 91/14413 | 10/1991 | WIPO . |
| 96/20831 | 7/1996 | WIPO . |

OTHER PUBLICATIONS

PCT Counterpart Search Report mailed Apr. 3, 1997.
*Absorbent Polymer Technology*, Lisa Brannon–Peppas and Ronald S. Harland (eds.), Elsevier, pp. 3–22, Sep., 1990.
BF Goodrich Specialty Polymers & Chemicals Division, Hystretch® Elastomer Emulsions, Doc. No. MSDS90.534, Nov. 2, 1990.
*Eastman AQ® Polymers Properties and Applications*, Eastman Chemicals Publication No. GN–389B, pp. 2–27, May, 1990.
Hoechst Celanese Corporation, *Material Safety Data Sheet*, MSDS No. 1101750318, pp. 1–3, Feb. 7, 1992.
"Preparation and Use of Composites Swellable by Water," *Chemical Abstracts*, vol. 114, No. 12, Abst. No. 114:10386m, Mar. 24, 1991.
"The Structure and Properties of Thixotropic Gels," *Chemical Abstracts*, vol. 30, No. 19, Oct. 10, 1936.
*Die Struktur und die Eigenschaften der thixotropen Gele*, Von B.S. Kandelaky, Kolloid Zeitschrift, V. 74, pp. 200–205, Feb., 1936.
*Principles of Colloid and Surface Chemistry*, Paul C. Hiemenz, 2nd ed., Marcel Dekker, Inc., pp. 782–783, Dec., 1985.
*Kirk–Othmer Encyclopedia of Chemical Technology*, 3rd ed., vol. 5, pp. 118–163, John Wiley & Sons, N.Y.–Chester–Brisbane & Toronto, Mar., 1979.
*Kirk–Othmer Encyclopedia of Chemical Technology*, 3rd ed., vol. 21, pp. 492–505, John Wiley & Sons, N.Y.–Chester–Brisbane & Toronto, Mar., 1983.
*The Condensed Chemical Dictionary*, 10th ed., Gessner G. Hawley, Van Nostrand Reinhold Co., N.Y., p. 838, est. Jul.–Aug., 1981.
*The Condensed Chemical Dictionary*, 10th ed., Gessner G. Hawley, Van Nostrand Reinhold Co., N.Y., p. 14, est. Jul., 1981.
*The Condensed Chemical Dictionary*, 11th ed., Gessner G. Hawley, Van Nostrand Reinhold Co., N.Y., pp. 567–568, 1987.
*Polymer Yearbook 3*, Richard A. Pethrick, Harwood Academic Publishers, Chur–London–Paris–New York, p. 65, Sep., 1986.

Primary Examiner—Rena Dye
Attorney, Agent, or Firm—Joseph P. Harps

[57] ABSTRACT

The present invention is directed toward a multilayer film which includes a first surface layer and a second surface layer. The first surface layer is composed of materials which disintegrate when subjected to conditions present in conventional sewage systems. The second surface layer is formed from a material which is essentially inert to water, urine and other bodily fluids. Typically, the second surface layer is an extremely thin coating which provides a waterproofing effect. The multilayer film may be utilized as an outer cover in a wide variety of products such as, for example, disposable diapers and feminine care products such as sanitary napkins. In one desirable embodiment the multilayer film includes only these two layers so that the material may be flushed down a conventional toilet without clogging the sewage system because the first surface layer rapidly disintegrates in water leaving only the thin, gossamer second surface layer which can pass through the sewage system without adversely affecting it.

26 Claims, No Drawings

U.S. PATENT DOCUMENTS

| | | | |
|---|---|---|---|
| 4,861,539 | 8/1989 | Allen et al. | 264/204 |
| 4,913,517 | 4/1990 | Arroyo et al. | 350/96.23 |
| 5,013,769 | 5/1991 | Murray et al. | 523/111 |
| 5,026,589 | 6/1991 | Schechtman | 604/372 |
| 5,056,960 | 10/1991 | Marienfeld | 405/270 |
| 5,225,489 | 7/1993 | Prevorsek et al. | 525/151 |
| 5,248,720 | 9/1993 | Deguchi et al. | 524/444 |
| 5,300,358 | 4/1994 | Evers | 604/372 |
| 5,317,037 | 5/1994 | Golden et al. | 523/128 |
| 5,318,552 | 6/1994 | Shiba et al. | 604/366 |
| 5,342,686 | 8/1994 | Guersen et al. | 428/378 |
| 5,466,518 | 11/1995 | Isaac et al. | 428/288 |

MULTILAYER HYDRODISINTEGRATABLE FILM

FIELD OF THE INVENTION

The field of the present invention is that of products which may conveniently be disposed of by flushing down a toilet and which will pass through a conventional sewage system without having an adverse impact on the system.

BACKGROUND OF THE INVENTION

For many years the problem of disposability has challenged the industries which provide disposable diapers, incontinent garments and feminine care products. While much headway has been made in addressing this problem, one of the weak links has been the inability to create an economical plastic material which will readily dissolve or disintegrate in water. See, for example, U.K. patent disclosure 2,241,373 and U.S. Pat. No. 4,186,233. Without such a product, the ability of the user to dispose of the product by flushing it down the toilet is greatly reduced, if not eliminated, as a result of the adverse impact the product would have on a conventional sewage system. Furthermore, the ability of the product to disintegrate in a landfill is quite limited because a large portion of the components of the product, which may well be biodegradable or photodegradable, are encapsulated in plastic which degrades over a long period of time, if at all. Accordingly, the larger the percentage of components which are degradable by natural forces and actions the more environmentally friendly the product. Therefore, increasing the amount of degradable components contained within a product has been a goal of those of skill in the art. More recently, a hydrodisintegratable material which is a blend of a water dispersible polymer, a xerogellant and a plasticizing agent has been developed. Such a material is disclosed in a U.S. patent application entitled "Hydrodisintegratable Material and Products Formed Thereby". The application was filed on Dec. 29, 1992, and has Ser. No. 07/997,797, pending.

Other related patent applications are U.S. patent application Ser. No. 08/046,064, U.S. Pat. No. 5,580,910, entitled "Self Sealing Film" which was filed on Apr. 12, 1993; U.S. patent application Ser. No. 08/107,490, U.S. Pat. No. 5,466, 518, entitled "Binder Compositions And Web Materials Formed Thereby" which was filed on Aug. 17, 1993; U.S. patent application Ser. No. 08/333,561, U.S. Pat. No. 5,496, 874, entitled "Moldable Hydrodisintegratable Material And Products Formed Thereby" which was filed on Nov. 2, 1994; U.S. patent application Ser. No. 08/443,300, abandoned, entitled "Moldable Hydrodisintegratable Material and Products Formed Thereby" which was filed on May 17, 1995; and U.S. patent application Ser. No. 08/446,373, U.S. Pat. No. 5,576,364, entitled "Binder Compositions and Web Materials Formed Thereby" which was filed on May 22, 1995. The entirety of all six (6) of these U.S. patent applications is hereby incorporated by reference.

Those of skill in the art will readily recognize that the satisfactory incorporation of such hydrodisintegratable materials into products such as, for example, disposable diapers and disposable feminine care products, is greatly enhanced if the hydrodisintegratable material is protected from contact with bodily fluids such as urine, saliva, perspiration, tears and menses which could undesirably trigger the hydrodisintegration of the product at a time prior to disposal. Such a situation would be clearly undesirable. However, in many products, the hydrodisintegratable material is somewhat protected from bodily fluids as a direct result of the product design. For example, disposable diapers are generally formed from an inner fluid permeable layer and outer fluid impermeable cover layer with an absorbent layer sandwiched therebetween. Exemplary diaper designs are disclosed in U.S. Pat. No. 5,295,986 to Zehner et al., U.S. Pat. No. 5,318,555 to Siebers et al., U.S. Pat. No. 5,192,606 to Proxmire et al., and U.S. Pat. No. 5,176,672 to Bruemmer et al. All of these patents are hereby incorporated by reference in their entirety.

In the case where the hydrodisintegratable material is used to form the outer cover of a disposable diaper, the hydrodisintegratable material is protected from insult or contact with urine by the absorbent structure contained within the diaper. That is the bodily fluid, urine, would have to pass through the absorbent structure before coming into contact with the outer cover of hydrodisintegratable material. Usually, for this to happen, the absorbent core of the disposable diaper would have to be saturated or the rate of the insult would have to be such that the absorbent capacity of the core is overwhelmed.

While the above design features can be utilized to generally protect the hydrodisintegratable material from bodily fluids, it is readily recognizable that the creation of a hydrodisintegratable material which is more resistant to disintegration in bodily fluids such as urine than water would be desirable. Such a hydrodisintegratable material would offer all the benefits of environmentally friendly disintegration while not being subject to premature hydrodisintegration as a result of an accidental contact with bodily fluids.

OBJECTS OF THE INVENTION

Accordingly, it is a general object of the present invention to provide a multilayer film having two surface layers where the first surface layer, in the presence of water, readily hydrodisintegrates and the second surface layer is highly inert, that is, is not hydrodisintegratable, in the presence of water.

It is another object of the present invention to provide a multilayer film which, if contacted by water on one surface thereof, rapidly hydrodisintegrates, while, if contacted by water on a second surface thereof, is highly resistant to hydrodisintegration.

Still further objects and the broad scope of applicability of the present invention will become apparent to those of skill in the art from the details given hereinafter. However, it should be understood that the detailed description of the presently preferred embodiment of the present invention is given only by way of illustration because various changes and modifications well within the spirit and scope of the invention will become apparent to those of skill in the art in view of the following description.

DEFINITIONS

As used herein, the term "xerogellant" refers to a material which, when in a substantially dry (less than 10 weight percent) state, has the ability to spontaneously imbibe (absorb) at least about twenty (20) times its own weight in distilled water having a pH of about 7. Importantly, the xerogellant should have the ability to generally retain its original identity after it has imbibed the fluid. For example, a bead, fiber or film formed from a xerogellant will still be recognizable as such after having imbibed the fluid. Xerogellants are well known to those in the art and are commonly referred to as "superabsorbent" materials. The twenty (20) times standard is achieved without any load being placed on the xerogellant and within a maximum time period of ten (10) minutes.

As used herein, the term "water dispersible polymer" refers to a polymeric material which is capable of forming a dispersion in an aqueous medium at ambient temperature (72 degrees Fahrenheit).

As used herein, the term "plasticizing agent" refers to an organic compound which, when added to a high polymer, may increase the ease of processing the high polymer or increase the toughness and flexibility of the high polymer after processing. A plasticizing agent may be able to accomplish all of these.

As used herein, the term "hydrodisintegratable" refers to a material which, in the presence of water, disintegrates into a particulate form where no individual particle is readily apparent to the unaided eye. Particles of this size generally have a maximum largest dimension of less than about one (1) millimeter.

As used herein, the term "thin film" refers to a film having an average thickness of less than about 50 mils. For example, the thin film may have an average thickness of less than about 25 mils. More particularly, the thin film may have an average thickness of less than about 10 mils. Even more particularly, the thin film may have an average thickness of less than 5 mils. In some instances, the thin film may have an average thickness of less than 1 mil.

Unless otherwise stated, average thickness is determined by five (5) random measurements of the film or a layer of the film and averaging the results.

As used herein, the term "high molecular weight" refers to any material having a number average molecular weight of at least 12,000. For example, the material may have a number average molecular weight of from about 14,000 to about 16,000.

As used herein, the term "substantially water impermeable" refers to a material which does not allow water to pass through it for ten (10) minutes. That is, the water impermeable material, upon being contacted by water and remaining in contact with the water, will not allow the water to pass through it during the ten (10) minute period. The contact angle of the water when measured by a contact angle goniometer, after ten (10) minutes, will be greater than or equal to 40 degrees.

As used herein, the term "snag test" refers to a test procedure developed and used by the National Sanitation Foundation (NSF) of Ann Arbor, Mich., to measure the time it takes a material to disintegrate under simulated sewage conditions. The test was slightly modified by us as noted below. The test is conducted by placing an about two (2) inch by about four (4) inch sample of plastic material on a hook shaped rod (modification-the test uses a straight rod) and stapling it to itself to form a loop to prevent it from slipping off (modification—the NSF procedure does nothing to insure the sample will stay on the rod/hook). The hook is lowered into a two (2) liter beaker of distilled water with a pH of about 7 and which is maintained at room temperature. The sample is stirred at 550 RPM. The time for the sample to break up and off the rod/hook is noted as well as the time required for the sample to disintegrate to a predetermined particle size.

SUMMARY OF THE INVENTION

The present invention is directed toward a multilayer film having a first surface layer and a second surface layer. Importantly, the first surface layer is formed from a hydrodisintegratable material which, in the presence of water, readily disintegrates. The material from which the first surface layer is formed includes from about 7.5 to about 85 weight percent of a water dispersible polymer; from about 7.5 to about 85 weight percent of a xerogellant and from about 7.5 to about 20 weight percent of a plasticizing agent.

In some embodiments the hydrodisintegratable material of the first surface layer may include from about 15 to about 75 weight percent of a water dispersible polymer; from about 15 to about 75 weight percent of a xerogellant and from about 10 to about 15 weight percent of a plasticizing agent. For example, the hydrodisintegratable material from which the first surface layer is formed may include from about 30 to about 60 weight percent of a water dispersible polymer; from about 30 to about 60 weight percent of a xerogellant and from about 10 to about 15 weight percent of a plasticizing agent. More particularly, the hydrodisintegratable material from which the first surface layer is formed may include from about 40 to about 50 weight percent of a water dispersible polymer; from about 40 to about 50 weight percent of a xerogellant and about 12 weight percent of a plasticizing agent.

In some embodiments the water dispersible polymer may be selected from the group including high molecular weight amorphous polyesters having one or more ionic substituents attached thereto.

In some embodiments the xerogellant may be selected from the group including starch grafted sodium polyacrylates.

In some embodiments the plasticizing agent may be selected from the group including glycerin, sorbitol, D-sorbitol, glucidol, sucrose, ethylene glycol, propylene glycol, diethylene glycol, polyethylene glycol, dimethyl acetamide, dimethyl sulfoxide, methyl pyrrolidene and tetramethylene sulfone.

The multilayer film also includes a second surface layer which is substantially water impermeable. That is, the second surface layer is formed from a material which is substantially inert to water and which provides a waterproofing function. In an embodiment where the multilayer film includes only two layers the second surface layer is joined directly to the first surface layer and performs the function of prohibiting water from penetrating through it and coming into contact with the first surface layer. Typically, the second surface layer is very thin in comparison to the first surface layer so that, once the first surface layer has hydrodisintegrated after being contacted with water, only an extremely thin gossamer material (the second surface layer) remains. For example, the thickness of the water impermeable second surface layer may comprise no more than 10% of the thickness of the multilayer film. More specifically, the thickness of the water impermeable second surface layer may comprise no more than 5% of the thickness of the multilayer film. Even more particularly, the thickness of the water impermeable second surface layer may comprise no more than 1% of the thickness of the multilayer film. For example, the thickness of the water impermeable second surface layer may comprise no more than 0.1% of the thickness of the multilayer film. That is, the thickness of the water impermeable second surface layer may comprise no more than 0.01% of the thickness of the multilayer film. In some desirable embodiments the water impermeable second surface layer has an average thickness of less than 0.001 inches. For example, the water impermeable second surface may have an average thickness of less than 0.0005 inches.

In one embodiment the material is formed into a thin film. The film is useful in the formation of disposable diapers and feminine care products which may be flushed down the toilet.

DETAILED DESCRIPTION OF THE INVENTION

The multilayer film of the present invention may be desirably formed in stages with the first stage being the compounding of the hydrodisintegratable material which will be used to form the hydrodisintegratable first surface layer. Thereafter, the compounded hydrodisintegratable material is formed into a film by conventional film-forming processes. It should be noted that, if the hydrodisintegratable film is brittle, as a result of being formed, for example, by conventional extrusion processes which can remove volatile materials such as water, the hydrodisintegratable film should be re-hydrated prior to further processing. Desirably, the hydrodisintegratable film is fully re-hydrated prior to any further processing. Hydration of the hydrodisintegratable film renders it more flexible, pliable and resistant to breakage and tearing. Thereafter, the water impermeable second surface layer is coated, sprayed or otherwise applied to the first hydrodisintegratable surface layer. Of course, with appropriate selection of materials, those of skill in the art will recognize that it may be possible to simultaneously form the first and second surface layers by conventional co-extrusion processes. In some embodiments, it may be desirable for the multilayer film to include additional layers which may be interspersed between the first hydrodisintegratable layer and the second water impermeable surface layer. Naturally, for the resultant product to be environmentally friendly, it is desirable for these layers to, likewise, be degradable.

The hydrodisintegratable first surface layer may be compounded by, for example, providing the components of the hydrodisintegratable first surface layer to a conventional twin screw extruder and allowing the extruder to effect the mixing and blending of the components in the proper proportions. If this method of compounding is utilized, the xerogellant and water dispersible polymer would desirably be provided to the compounding extruder in particulate form. Typically, xerogellants are available in particulate form which, in some instances, is a fine powder. The plasticizing agent may desirably be added to the compounding extruder in fluid (liquid) form.

While any material meeting the definition of a xerogellant may be utilized, exemplary xerogellants include sodium carboxymethyl cellulose, derivatives of sodium carboxymethyl cellulose, poly(acrylic acid) salts, (ethylene oxide), acrylonitrile-grafted starch, hydrolyzed polyacrylonitrile, poly(vinyl alcohol-sodium acrylate) and polyisobutylene-co-disodium maleate. One desirable xerogellant is a starch grafted sodium polyacrylate which may be obtained from Hoechst Celanese Corporation under the trade designation Sanwet IM5000. Hoechst Celanese literature describe Sanwet IM5000 as a starch grafted sodium polyacrylate having a specific gravity of about 0.57; a moisture content of about 5%; and a pH of about 6.3. The material is white in appearance and is provided as a granular powder.

While any film forming water dispersible polymer may be utilized, exemplary film forming water dispersible polymers include such polymers chosen from the group including high molecular weight amorphous polyesters having one or more ionic substituents attached thereto. This type of polymer is available in pellet form from the Eastman Kodak Co. of Rochester, N.Y. under the trade designation Eastman AQ. In particular, Eastman AQ 29S, AQ 38S and AQ 55S. The numerical designation of the AQ polymers refers to the polymer's dry glass transition temperature (in degrees C.). Eastman Kodak literature states that AQ polymers are relatively high molecular weight, amorphous polyesters that disperse directly in water without the assistance of organic cosolvents, surfactants, or amines. This water dispersibility is attributable, in large part, to the presence of ionic substituents attached to the polymer chain which is illustrated below.

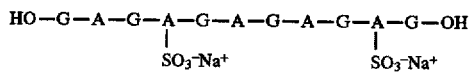

where

A = an aromatic dicarboxylic acid moiety
G = an aliphatic or cycloaliphatic glycol residue
OH = hydroxy end groups The literature continues by stating that some of the aromatic dicarboxylic acid units in Eastman AQ polymer chains have sodiosulfo ($SO_3^-Na^+$) substituents. Although only two are shown in the simplified structure above, on the average, there are five to eight ionic sodiosulfo substituents per molecule.

Alternatively, the water dispersible polymer may be selected from the group including elastomeric emulsions, acrylic polymers, polyoxides, vinyl polymers, cellulose derivatives, starch derivatives, polysaccahrides, proteins and copolymers thereof. Exemplary elastomeric emulsions may be obtained from the B.F. Goodrich Co., Specialty Polymers & Chemicals Division under the trade designation HyStretch. HyStretch elastomeric emulsions typically are a blend of about 50% latex, about 50% water, less than about 0.01% acrylamide, less than about 1.0% ammonium hydroxide, less than about 0.01% ethyl acrylate, less than about 0.1% formaldehyde and less than about 0.0025% N-methylolacrylamide.

While any suitable plasticizing agent may be utilized, exemplary plasticizing agents include glycerin, sorbitol, D-sorbitol, glucidol, sucrose, ethylene glycol, propylene glycol, diethylene glycol, polyethylene glycol, dimethyl acetamide, dimethyl sulfoxide, methyl pyrrolidene and tetramethylene sulfone. One exemplary plasticizing agent is D-sorbitol which may be obtained from the Fisher Scientific Co. of Fair Lawn, N.J., under the trade designation S459.

After the three components have been thoroughly mixed by the compounding extruder, in conventional manner, they are extruded in a raw, unformed condition. The xerogellant, the film forming water dispersible polymer and the plasticizing agent are blended together in a conventional manner so that the final weight percentage of these components, is from about 7.5 to about 85 weight percent of the water dispersible polymer; from about 7.5 to about 85 weight percent of the xerogellant; and from about 7.5 to about 20 weight percent of the plasticizing agent. More particularly, the weight percentages of these components of the material may range from about 15 to about 75 weight percent of the water dispersible polymer; from about 15 to about 75 weight percent of the xerogellant; and from about 10 to about 15 weight percent of the plasticizing agent. Even more particularly, the final weight percentages of these components may range from about 30 to about 60 weight percent of the water dispersible polymer; from about 30 to about 60 weight percent of the xerogellant; and from about 10 to about 15 weight percent of the plasticizing agent. Yet even more particularly, the final weight percentages of these components may range from about 40 to about 50 weight percent of a water dispersible polymer; from about 40 to about 50 weight percent of a xerogellant; and about 12 weight percent of the plasticizing agent.

In some embodiments it may be desirable to employ various additives such as antioxidants, antistatic agents, blowing agents, compatibilizers, flame retardants, heat stabilizers, impact modifiers, lubricants, ultraviolet stabilizers, processing aids, surfactants, dispersants, slip agents, etc., as fabricating agents or as modifiers depending on the specific properties which would be desirable to have in the final product.

The use of surfactants can further enhance the rate of hydrodisintegration of the film. Exemplary surfactants which can be utilized in the invention are (1) anionic surfactants such as carboxylic acids and salts, sulfonic acids and salts, sulfuric acid esters and salts, phosphoric and polyphosphoric acid esters and salts; (2) non-ionic surfactants such as ethoxylated alcohols, ethoxylated alhylphenols, ethoxylated carboxylic esters and ethoxylated carboxylic amides; (3) cationic surfactants such as oxygen free amines, oxygen containing amines, amide linked amines and quaternary ammonium salts; and (4) amphoteric surfactants such as imidazolinium derivatives, amino acids and their derivatives in which the nitrogen atom is protonated and alkylketaimes.

The surfactants may be added so that they form from at least about 0.01 to about 0.10 weight percent of the hydrodisintegratable first surface layer. For example, the surfactants may form from at least about 0.03 to about 0.08 weight percent of the hydrodisintegratable first surface layer. More particularly, the surfactants may form from at least about 0.05 to about 0.06 weight percent of the hydrodisintegratable first surface layer.

Those of skill in the art will readily recognize that the hydrodisintegratable material may be compounded by other conventional methods.

After the hydrodisintegratable material has been compounded, the material may then be formed into a thin film. This also may be accomplished by conventional film extrusion processes or conventional film casting processes. Any other applicable conventional film forming process will also suffice.

Lastly, the water impermeable second surface layer is applied by conventional methods such as by being sprayed on. Other methods, for applying the water impermeable second surface layer may also be utilized. These include, for example, nip coating, brushing and laminating. Of course, if the material used to form the second surface layer may be extruded, the first and second surface layers may be coextruded as a two layer multilayer film. If desirable, other layers may be coextruded between the first and second surface layers.

While any material which will form a substantially water impermeable layer may be used to form the water impermeable second surface layer, one desirable material is an acrylic material which may be sprayed onto the first hydrodisintegratable surface layer. The acrylic material may be obtained from the Dayton Electric Mfg. Co. of Chicago, Ill., under the trade designation Dem Kote 2X723B Clear Plastic Industrial Spray.

Those of skill in the art will recognize that for the multilayer material to be flushable down a conventional toilet, the second, water impermeable surface layer should be as thin as practicable while still being able to perform the function of protecting the hydrodisintegratable first surface layer from the ravages of water. To this effect, it is desirable that the thickness of the water impermeable second surface layer may comprise no more than 10% of the thickness of the multilayer film. More specifically, the thickness of the water impermeable second surface layer may comprise no more than 5% of the thickness of the multilayer film. Even more particularly, the thickness of the water impermeable second surface layer may comprise no more than 1% of the thickness of the multilayer film. For example, the thickness of the water impermeable second surface layer may comprise no more than 0.1% of the thickness of the multilayer film. That is, the thickness of the water impermeable second surface layer may comprise no more than 0.01% of the thickness of the multilayer film. In some desirable embodiments the water impermeable second surface layer has an average thickness of less than 0.001 inches. For example, the water impermeable second surface may have an average thickness of less than 0.0005 inches.

The invention will now be described with respect to certain specific embodiments thereof.

EXAMPLES

Preparation of Hydrodisintegratable Compound

A hydrodisintegratable compound from which the hydrodisintegratable layer of the multilayer film would be formed was first prepared.

A co-rotating, intermeshing, seven zone, twin screw extruder having both polymer and pellet feed mechanisms was selected as the equipment of choice for the compounding process. The self-wiping design of the twin screw with its superior transport properties results in improved dispersion (blending) of the components of the composition while still subjecting the composition to less shear stress. Utilization of a twin screw extruder is more desirable than a single screw extruder because, generally speaking, twin screw extruders subject the extruded material to less shear stress than single screw extruders. Shear is desirably minimized due to the fact that some materials such as, for example, sulfonated polyesters, are shear sensitive. Furthermore, twin screw extruders are generally known for their excellent mixing characteristics and their ability to accept gas, liquid or solid feed materials at any point along the extruder length.

The plasticizing agent utilized was D-sorbitol. The D-sorbitol was made up as an eighteen (18) percent solution in water.

The water dispersible polymer utilized may be obtained from Eastman Chemical Co. in pellet form under the trade designation AQ 38S. Eastman literature states that AQ 38S has an approximate number average molecular weight of 14,000; a hydroxyl number of less than 10; an acid number of less than 2; a glass transition ($T_g$) of about 38 degrees Celsius; a melt viscosity of 9,700 poise at 200 degrees C. (392 degrees F.) when measured by Sieglaff-McKelvey Capillary Rheometer, (100 $sec^{-1}$ shear rate) and a clear, light amber color.

The xerogellant utilized may be obtained in powder form from Hoechst Celanese Corporation under the trade designation Sanwet IM5000. Sanwet IM5000 is a starch grafted sodium polyacrylate. Hoechst Celanese literature describes IM5000 as having a specific gravity of about 0.57; a moisture content of about 5%; and a pH of about 6.3. The material is white in appearance and is provided as a granular powder.

The twin screw extruder had the following process parameters:

|  | Zone: | | | | | |
| --- | --- | --- | --- | --- | --- | --- |
|  | 1 | 2 | 3 | 4 | 5 | 6 |
| Actual Extruder Zone Temps. (degrees C.): | 96/ | 96/ | 101/ | 118/ | 115/ | 110 |

| Screw rpm: | 150 | | |
| --- | --- | --- | --- |
| Torque: | 74–91% | zone 1: | AQ 38S and Sanwet IM5000 feed |
| Pressure: | 210 psi. (no die) | zone 2: | D-sorbitol Solution feed |
| Head Temp: | 110 degrees Centigrade (C.) | zone 6: | Vacuum applied |
| Vacuum: | 23 in Hg. | | |

An adequate amount of both AQ 38S and Sanwet IM5000 was provided to the hoppers feeding the twin screw extruder at zone 1. Feed rates of 50 grams per minute were obtained for both the AQ 38S and the Sanwet IM5000 in order to obtain a 50/50 water dispersible polymer/xerogellant blend.

The 18% D-sorbitol solution was provided at zone 2. This solution was pumped into the extruder at zone 2 using a Neptune proportioning pump. A solution feed rate of 125 grams of D-sorbitol solution per minute was utilized.

The die was removed from the end of the extruder to allow for easier sample flow from the end of the barrel.

A vacuum was drawn on the sample at zone 6 in order to remove excess water.

The sample was extruded as a one and one-half inch wide strip and about 0.25 inch in thickness.

The approximate composition of the materials fed into the extruder was: (1) 22.2 weight percent AQ 38S; (2) 22.2 weight percent Sanwet IM5000; (3) 10.0 weight percent D-sorbitol; and (4) 45.6 weight percent water.

After extrusion, including water removal at zone 6, the approximate composition of the hydrodisintegratable material formed was: (1) 43 weight percent AQ 38S; (2) 43 weight percent Sanwet IM5000; (3) 10 weight percent D-sorbitol; and (4) 4 weight percent water.

Extrusion of the Hydrodisintegratable Film Layer

The hydrodisintegratable composition was next formed into a film by conventional extrusion techniques. The extruder utilized to form the hydrodisintegratable composition into a film was a model KTS-125 1¼ inch single screw extruder with L/D of 24:1 and a five (5) horsepower motor. This extruder has a serial number of 14498. The extruder was manufactured by Killion Extruders, Inc. of Cedar Grove, N.J. The KTS extruder was equipped with a four (4) inch tape die which was used to shape the hot extrudate. The die was set up for ribbon tape with air cooling. The screw utilized during extrusion had a thread depth in the feed section of 0.310 inches for eight (8) flights. The screw then tapers for eight (8) more flights. The thread depth in the metering section of the screw is 0.070 inches for eight (8) flights. This screw therefore has an overall compression ration of 3:1.

Three (3) film-forming runs were performed. The temperature through the extruder was as follows for each run.

|  | Zone: | | | | | | |
| --- | --- | --- | --- | --- | --- | --- | --- |
|  | 1 | 2 | 3 | 4 | 5 | Die | Melt |
| RUN I | | | | | | | |
| Actual Extruder Zone Temps. (F.): | 190/ | 225/ | 220/ | 220/ | 220/ | 210/ | 212 |
| Screw rpm: 20 | | | | | | | |
| Amps: 2.5 | | | | | | | |
| Pressure: 400 pounds per square inch, gauge (psi, g) | | | | | | | |
| A ten (10) mil thick film was formed in this run. | | | | | | | |
| RUN II | | | | | | | |
| Actual Extruder Zone Temps. (F.): | 200/ | 235/ | 235/ | 230/ | 230/ | 220/ | 232 |
| Screw rpm: 20 | | | | | | | |
| Amps: 4.0 | | | | | | | |
| Pressure: 600 psi, g | | | | | | | |
| A nine (9) mil thick film was formed in this run. | | | | | | | |
| RUN III | | | | | | | |
| Actual Extruder Zone Temps. (F.): | 210/ | 245/ | 245/ | 240/ | 240/ | 230/ | 243 |
| Screw rpm: 20 | | | | | | | |
| Amps: 4.5 | | | | | | | |
| Pressure: 800 psi, g | | | | | | | |

A nine (9) mil thick film was formed in this run.

Observations during the actual extrusion included the fact that bridging in the feed hopper was present and that starve feeding was needed in order for the process to be performed properly. Additionally, the comment was made that films as thin as five (5) mils in thickness could be run if the temperature profile was good.

Formation of the Multilayer Film

Because the films formed in the second extrusion process were quite brittle due to the removal of volatiles (water) during the process, the films were first re-hydrated to a point where the total volatiles was 14 weight percent. Re-hydration was accomplised by placing the film in a container at 70° C. and 100% relative humidity for approximately four (4) hours. This is the point of maximum hydration of the films.

The multilayer film of the present invention was formed by spraying a clear acrylic coating onto the rehydrated samples obtained from the three (3) runs described above. The acrylic material may be obtained from the Dayton Electric Mfg. Co. of Chicago, Ill., under the trade designation Dem Kote 2X723B clear plastic industrial spray. The coating thickness was assumed to be approximately 0.0003 inches. Due to irregularities in the surface of the hydrodisintegratable film layer, the thickness of the coating was not directly measured after it had been applied to the hydrodisintegratable film. The thickness of the coating layer was estimated by evenly spraying the acrylic coating material onto an aluminum foil sheet from a distance of about 4 inches for about 0.25 seconds and then measuring the thickness of the applied coating. Four (4) such coats were applied to the aluminum foil with twenty (20) minutes of drying time between each spraying. Thereafter, the average of the five measurements of the coating on the aluminum foil was 0.0003 inches. (The foil was measured before and after the coating process.) Then the same procedure was followed to coat the hydrodisintegratable film layer and the thickness of the coating was assumed to be the same as that on the foil.

Experimental Results

A series of trials was performed to determine whether the application of the acrylic coating adversely affected the ability of the hydrodisintegratable layer of the film to hydrodisintegrate.

Control in Water

An uncoated film sample was subjected to snag testing in water. The sample was immersed in water in accordance with the snag test. At eight minutes and fifty seconds (8:50) the first small bits of film began to break away. These particles were approximately the size of fine sand granules. At fifteen minutes and twenty seconds (15:20) larger particles began to break away from the film. At nineteen minutes and fifty-one seconds (19:51) large pieces of film began to break away. These pieces varied in size. At twenty four minutes and forty two seconds (24:42) the film broke free of the rod holding it and the trial was ended.

Trial in Water

A coated film sample was subjected to snag testing in water in accordance with the snag test. The sample was immersed in water. At five minutes and thirteen seconds (5:13) the first small bits of film began to break away. These particles were approximately the size of fine sand granules. These bits broke away from the inside (uncoated side) of the film. At fifteen minutes and thirty seconds (15:30) larger particles began to break away from the film. These particles, which also broke away from the inside (uncoated side) of the film were approximately the size of snowflakes. At twenty one minutes and thirty seven seconds (21:37) large pieces of material began to break away. These pieces varied in size and also broke away from the inside (uncoated side) of the film. At one hour and fifteen minutes (1:15:00) all of the material of the inside (uncoated side) of the film had broken away from the acrylic coating. However, the acrylic coating had not separated from the rod holding it. The trial was ended at this point.

Control in Synthetic Urine

An uncoated film sample was subjected to snag testing in synthetic urine. The synthetic urine may be purchased from PPG Industries Inc. of Appleton, Wis. under the trade designation CSI. The sample was immersed in accordance with the snag test. However, synthetic urine was substituted for the water. At twelve minutes and twenty one seconds (12:21) the first small bits of film began to break away. These particles were approximately the size of fine sand granules. At twenty four minutes and thirty eight seconds (24:38) larger particles began to break away from the film. At twenty six minutes and nine seconds (26:09) large pieces of film began to break away. These pieces varied in size. At twenty eight minutes and twenty three seconds (28:23) the film broke free of the rod holding it and the trial was ended.

Trial in Synthetic Urine

A coated film sample was subjected to snag testing in synthetic urine. The sample was immersed in accordance with the snag test. Synthetic urine was substituted for the water. At twelve minutes and twenty seconds (12:20) the first small bits of film began to break away. These bits were approximately the size of fine sand granules. These bits broke away from the inside (uncoated side) of the film. At twenty seven minutes and ten seconds (27:10) larger particles began to break away from the film. These particles, which also broke away from the inside (uncoated side) of the film were approximately the size of snowflakes. At thirty one minutes and twenty nine seconds (31:29) large pieces of material began to break away. These pieces varied in size and also broke away from the inside (uncoated side) of the film. At thirty four minutes and six seconds (34:06) the film broke free of the rod holding it and the trial was ended.

The above trials generally demonstrate that there is no significant difference in the time (rate) of hydrodisintegration of the hydrodisintegratable layer of the multilayer film as compared to the hydrodisintegration of a control, uncoated layer of the hydrodisintegratable material. It should be noted that in the trial of the multilayer film in water, the coating layer did cling to the snag test hook throughout the trial. One feature of the present invention which is highlighted by the data is that, generally speaking, the hydrodisintegratable layer was more resistant to disintegration in synthetic urine as compared to water. This feature is desirable when the multilayer film is to be used as an outer cover for a disposable diaper with the coating layer forming the outer surface of the diaper. Thus, in the event that a urine insult overwhelms the absorbent core of the diaper and contacts the hydrodisintegratable inner surface layer of the diaper outer cover, the layer will resist disintegration for a significant period of time. This time period is typically enough to allow the absorbent core to absorb the excess urine which was initially presented at too fast a rate to be absorbed.

Additional testing was carried out to demonstrate that the acrylic layer provides adequate protection against fluid contacting the hydrodisintegratable layer of the multilayer film where the fluid insult to the multilayer film arises on the surface of the multilayer film which is formed by the acrylic material. That is to say, this testing was directed at proving that the sprayed-on acrylic coating layer was a water impermeable layer as defined by the present application. A good means of proving water impermeability is to measure the contact angle of a drop of water placed on the surface of a material. The greater the contact angle, the greater the resistance of the material to penetration by water.

A drop of water was carefully placed upon the sprayed-on acrylic coating surface of a sample of the multilayer film using a #24 needle and a Popper and Sons 1 cc tuberculin syringe. The drop was approximantly 1/20 cc in volume. The contact angle was measured over a ten minute time period. The results are reported in Table I.

TABLE I

| TIME IN MINUTES | CONTACT ANGLE |
|---|---|
| 0 | 57 degrees |
| 3 | 49 degrees |
| 10 | 46 degrees |

All contact angles were measured using a contact angle goniometer model 100-00 MRL manufactured by Rame'-Hart, Inc. of Mountain Lakes, N.J. It is believed that the decrease in the measured value of the contact angle over the ten (10) minute time period is due to evaporation of the water.

While the invention has been described in detail with respect to specific preferred embodiments thereof, it will be appreciated that those skilled in the art, upon attaining an understanding of the foregoing, may readily conceive of alterations to and variations of the preferred embodiments. Such alterations and variations are believed to fall within the scope and spirit of the invention and the appended claims.

What is claimed is:

1. A multilayer film having an average thickness of less than about 50 mils, the film comprising:
   a hydrodisintegratable first surface layer film comprising:
      from about 7.5 to about 85 weight percent of a water dispersible polymer;
      from about 7.5 to about 85 weight percent of a xerogellant; and
      from about 7.5 to about 20 weight percent of a plasticizing agent; and
   a substantially water impermeable second surface layer film comprising no more than 5% of the thickness of the multilayer film.

2. The multilayer film of claim 1, wherein the hydrodisintegratable layer comprises:
   from about 15 to about 75 weight percent of a water dispersible polymer;
   from about 15 to about 75 weight percent of a xerogellant; and
   from about 10 to about 15 weight percent of a plasticizing agent.

3. The multilayer film of claim 1, wherein the hydrodisintegratable layer comprises:
   from about 30 to about 60 weight percent of a water dispersible polymer;
   from about 30 to about 60 weight percent of a xerogellant; and
   from about 10 to about 15 weight percent of a plasticizing agent.

4. The multilayer film of claim 1, wherein the hydrodisintegratable layer comprises:
   from about 40 to about 50 weight percent of a water dispersible polymer;
   from about 40 to about 50 weight percent of a xerogellant; and
   about 12 weight percent of a plasticizing agent.

5. The multilayer film of claim 1, wherein the water dispersible polymer is selected from the group consisting of high molecular weight amorphous polyesters having one or more ionic substituents attached thereto.

6. The multilayer film of claim 1, wherein the xerogellant is selected from the group consisting of starch grafted polyacrylates.

7. The multilayer film of claim 1, wherein the plasticizing agent is selected from the group consisting of glycerin, sorbitol, D-sorbitol, glucidol, sucrose, ethylene glycol, propylene glycol, diethylene glycol, polyethylene glycol, dimethyl acetamide, dimethyl sulfoxide, methyl pyrrolidene and tetramethylene sulfone.

8. The multilayer film of claim 1, wherein the water impermeable surface layer comprises no more than 1% of the thickness of the multilayer film.

9. The multilayer film of claim 1, wherein the water impermeable surface layer comprises no more than 0.1% of the thickness of the multilayer film.

10. The multilayer film of claim 1, wherein the water impermeable surface layer comprises no more than 0.01% of the thickness of the multilayer film.

11. The multilayer film of claim 1, wherein the water impermeable surface layer has an average thickness of less than 0.001 inches.

12. The multilayer film of claim 1, wherein the water impermeable surface layer has an average thickness of less than 0.0005 inches.

13. The multilayer film of claim 1, wherein the film consists of two layers.

14. The multilayer film of claim 1, wherein the hydrodisintegratable first surface layer is more resistant to disintegration in synthetic urine than in water.

15. A thin multilayer film having an average thickness of less than about 50 mils, the film comprising:
   a hydrodisintegratable first surface layer film comprising:
      from about 7.5 to about 85 weight percent of a water dispersible polymer selected from the group consisting of high molecular weight amorphous polyesters having one or more ionic substituents attached thereto;
      from about 7.5 to about 85 weight percent of a xerogellant selected from the group consisting of starch grafted polyacrylates; and
      from about 7.5 to about 20 weight percent of a plasticizing agent selected from the group consisting of glycerin, sorbitol, D-sorbitol, glucidol, sucrose, ethylene glycol, propylene glycol, diethylene glycol, polyethylene glycol, dimethyl acetamide, dimethyl sulfoxide, methyl pyrrolidene and tetramethylene sulfone; and
   a substantially water impermeable second surface layer film comprising no more than 5% of the thickness of the multilayer film.

16. The multilayer film of claim 15, wherein the film consists of two layers.

17. The multilayer film of claim 15, wherein the water impermeable surface layer comprises no more than 1% of the thickness of the multilayer film.

18. The multilayer film of claim 15, wherein the water impermeable surface layer comprises no more than 0.1% of the thickness of the multilayer film.

19. The multilayer film of claim 15, wherein the water impermeable surface layer comprises no more than 0.01% of the thickness of the multilayer film.

20. A multilayer film having an average thickness of less than about 50 mils, the film comprising:
   a hydrodisintegratable first surface layer film comprising:
      from about 7.5 to about 85 weight percent of a water dispersible polymer selected from the group consisting of high molecular weight amorphous polyesters having one or more ionic substituents attached thereto;
      from about 7.5 to about 85 weight percent of a xerogellant selected from the group consisting of starch grafted polyacrylates; and
      from about 7.5 to about 20 weight percent of D-sorbitol; and
   a substantially water impermeable second surface layer film having an average thickness of less than 0.0005 inches; and
   wherein the substantially water impermeable second surface layer film comprises no more than 5% of the thickness of the multilayer film.

21. The multilayer film of claim 20, wherein the film consists of two layers.

22. The multilayer film of claim 20, wherein the hydrodisintegratable layer is more resistant to disintegration in urine than in water.

23. The multilayer film of claim 20, wherein the water impermeable surface layer comprises no more than 1% of the thickness of the multilayer film.

24. The multilayer film of claim 20, wherein the water impermeable surface layer comprises no more than 0.1% of the thickness of the multilayer film.

25. The multilayer film of claim 20, wherein the water impermeable surface layer comprises no more than 0.01% of the thickness of the multilayer film.

26. The multilayer film of claim 15, wherein the hydrodisintegratable layer is more resistant to disintegration in urine than in water.

* * * * *